US005908785A

United States Patent [19]

Washburn et al.

[11] Patent Number: 5,908,785

[45] Date of Patent: Jun. 1, 1999

[54] COMPOSITIONS AND METHODS FOR USE IN CONTROLLING INSECT POPULATIONS

[75] Inventors: Jan Oliver Washburn, Berkeley; Loy Elaine Volkman, Richmond, both of Calif.

[73] Assignee: The Regents of the University of California, Oakland, Calif.

[21] Appl. No.: 08/871,011

[22] Filed: Jun. 6, 1997

Related U.S. Application Data

[63] Continuation of application No. 08/489,522, Jun. 12, 1995, abandoned.

[51] Int. Cl.[6] ................................ C12N 5/06; C12N 7/01

[52] U.S. Cl. .................. 435/456; 435/320.1; 435/235.1; 514/44; 536/23.2; 536/23.72; 424/93.1; 424/93.2; 935/32; 935/9; 935/10; 935/34; 935/52

[58] Field of Search ............................ 435/320.1, 235.1, 435/172.3, 456; 514/44; 424/93.1, 93.2; 536/23.2, 23.72; 935/9, 10, 32, 34, 52

[56] References Cited

U.S. PATENT DOCUMENTS

| | | | |
|---|---|---|---|
| 4,879,236 | 11/1989 | Smith et al. | 35/320.1 |
| 5,011,685 | 4/1991 | Granados | 424/93.6 |
| 5,162,222 | 11/1992 | Guarino et al. | 435/348 |

OTHER PUBLICATIONS

Dunphy, G.B. and Thurston, G.S., Entomopatho–Genic Nematodes in Biological Control, pp. 301–323.

Dib–Hajj et al. 1993 Proc. Natl. Acad. Sci. USA 90: 3765–3769.

Watson et al. (1987) in: Molecular Biology of the Gene, fourth edtion, Benjamin Cummings Publ. Co. Menlo Park, CA, p. 313.

Webster's II New Riverside University Dictionary, 1984, Soukhanov et al., eds., Houghton Mifflin Company, Boston MA pp. 631 and 878.

Vail, P. V. and S. S. Collier. 1982. Comparative replication, mortality, and inclusion body production of the *Autographa californica* Nuclear Polyhedrosis Virus in *Heliothis* sp. *Ann. Entomol. Soc. Am.* 75:376–382.

Vail, P. V. and Vail, S. V. 1987. Comparative replication of *Autographa californica* nuclear polyhedrosis virus in tissues of *Heliothis* spp. (Lepidoptera: Noctuidae). *Ann. Entomol. Soc. Amer.* 80:734–738.

Bonning, B. C. and Hammock, B. D. 1992. Development and potential of genetically engineered viral insecticides. *Biotechnology and Genetic Engineering Reviews* 10:455–489.

Maeda, S. 1994. Expression of foreign genes in insect cells using baculovirus vectors, pp. 1–31. In (K. Maramorosch and A. H. McIntosh, eds.), *Insect Cell Biotechnology,* CRC Press, Boca Raton, FL.

Saul, S.J. and Sugumaran, M. 1988. Prophenol oxidase activation in the hemolymph of *Sarcophaga bullata* larvae. *Arch. Insect Biochem. and Physiol.* 7:91–104.

Vinson, S. B. 1990. How parasitoids deal with the immune system of their host: an overview. *Arch. Insect Biochem. and Physiol.* 13:3–27 1990.

Blissard, G.W., Theilmann, D.A. and Summers, M.D. 1980. Segment W of *Campoletis sonorensis* virus, expression, gene products and organization. *Virology* 89:78–89.

Theilmann, D.A. and Summers, M.D. 1988. Identification and comparison of *Campoletis sonorensis* virus transcripts expressed from four genomic segments in the insect hosts *Campoletis sonorensis* and *Heliothis virescens. Virology* 167:329–341.

Faulkner P. (1982) A novel class of wasp viruses and insect immunity Nature 299:490.

Engelhard, E. K., Kam–Morgan, L. N. W., Washburn, J. O., and Volkman, L. E. 1994. The insect tracheal system: a conduit for the systemic spread of *Autographa californica* M nuclear polyhedrosis virus. *Pros. Natl. Acad. Sci. USA* 91:3224–3227.

Engelhard, E. K., Keddie, B. A., and Volkman, L. E. 1991. Isolation of third, fourth and fifth instar larval midgut epithelia of the moth, *Trichoplusia ni. Tissue and Cell* 23, 917–928.

Li, X. and B.A. Webb (1994). Apparent functional role for a cystein–rich polydnavirus protein in suppression of the insect cellular immune response. J. of Virol. 68, 7482–7489.

Maeda, S.(1995) Further development of recombinant baculovirus insecticies. Current Opinion in Biotechnology 6:313–319.

Edson, K.M., Vinson, S.B., Stoltz, D.B., and M.D. Summers. (1981) Virus in a parasitid wasp: supression of the celular immune response of the parasitoid's host. Science 211:582–583.

*Primary Examiner*—Christopher S. F. Low
*Attorney, Agent, or Firm*—Townsend and Townsend and Crew

[57] ABSTRACT

Compositions and methods for use in controlling insect populations, including a first agent which suppresses insect immune function of a target insect in conjunction with a second agent which is an insect pathogen for the target insect. Preferably, the first agent is a polypeptide having immunosuppressive activity in the target insect or a polynucleotide sequence encoding the polypeptide; in the latter case, the polynucleotide may be conveniently administered to the target insect in a vector comprising the second agent (e.g., AcMNPV or similar insect pathogen).

16 Claims, 3 Drawing Sheets

COMPOSITIONS AND METHODS FOR USE IN CONTROLLING INSECT POPULATIONS

This a Continuation of application Ser. No. 08/489,522, filed Jun. 12, 1995 now abandoned, the disclosure of which is incorporated by reference.

BACKGROUND OF THE INVENTION

This invention relates generally to the fields of biology and chemistry. More particularly, the present invention relates to compositions and methods for use in control (e.g., reduction or elimination) of insect populations.

In view of the serious damage to plants and animals induced by some species thereof, there is tremendous interest in identifying compositions and methods for control of insect populations. Obvious problems with respect to the use of some organic and inorganic chemical insecticides have directed attention to the development of other approaches. One such alternative approach involves the identification of microbial insecticides which might be more species-specific than some heretofore-known chemical insecticides. Of particular interest in this regard are baculoviruses (Baculoviridae).

Two major factors pose significant barriers for the practical development of baculoviruses as microbial insecticides for use in programs aimed at numerically reducing populations of insect pests. First, most species of virus produce fatal infections in only a small group of closely related host species. This life history feature makes these insect pathogens environmentally safe for humans and other nontarget species, but it significantly limits the kinds of pests that can be controlled effectively. Second, infected hosts require a considerable amount of time to succumb, and during the interval between initial infection and death, the larvae continue to feed and to cause significant economic damage.

*Autographa californica* M Nucleopolyhedrosis Virus (AcMNPV) is the best studied of the baculoviruses and is known to infect the larvae of approximately 30 species in several families within the insect order, Lepidoptera [Granados, R. R., and Williams, K. A. (1986). In vivo infection and replication of baculoviruses. In *The biology of baculoviruses* (eds. R. R. Granados and B. A. Federici) vol. I, CRC Press, Inc., Boca Raton, Fla.]. Infections are initiated when larvae ingest virion-containing proteinaceous occlusions (polyhedra) which rapidly dissolve upon contact with the highly alkaline juices within the larval midgut. Dissolution releases the enveloped occlusion-derived virus (ODV) [Murphy, F. A., Fauquet, C. M., Bishop, D. H. L., Ghabrial, S. A., Jarvis, A. W., Martelli, G. P., Mayo, M. P., and Summers, M. D. (1995). *Virus Taxonomy: sixth report of the international committee on taxonomy of viruses.* Springer Verlag, Wien, N.Y.] which may contain as many as 29 individual nucleocapsids [Adams, J. R. and Mclintock, J. T. (1991). Baculoviridae. Nuclear polyhedrosis viruses. Part 1. Nuclear polyhedrosis viruses of insects. *In Atlas of invertebrate viruses* (eds. J. R. Adams and J. R. Bonami), CRC Press, Inc., Boca Raton, Fla.]. Nucleocapsids enter differentiating and mature columnar cells in the midgut epithelium following fusion of the viral envelope with the microvillar membrane of these cells [Kawanishi, C. Y., Summers, M. D., Stoltz, D. B., and Arnott, H. J. 1972. Entry of an insect virus in vivo by fusion of viral envelope and microvillus membrane. *J. Invertebr. Pathol.* 20:104–108; Granados, R. R. 1978. Early events in the infection of *Heliothis zea* midgut cells by a baculovirus. *Virology* 90:170–174]. Nucleocapsids then migrate to the nucleus where they uncoat and begin the processes of transcription and replication. Evidence suggests that some parental nucleocapsids also may be transported directly through the cell where they are re-enveloped by budding through a modified basal plasma membrane [Granados, R. R., and Lawler, K. A. 1981. In vivo pathway of *Autographa californica* baculovirus invasion and infection. *Virology* 108, 297–308].

Progeny nucleocapsids produced by infected midgut cells also bud from the basal plasma membrane containing a newly synthesized, viral-encoded glycoprotein, gp64 [Keddie, B. A., Aponte, G. W., and Volkman, L. E. 1989. The pathway of infection of *Autographa californica* nuclear polyhedrosis virus in an insect host. *Science* 243, 1728–1730]. This budded virus (BV) spreads infection to the other tissues of the insect which produce both BV aid polyhedra. Insects die after virtually all their tissues are infected massively, and cadavers liquefy releasing numerous polyhedra which horizontally transmit the virus to susceptible larvae.

Although many species of lepidopteran larvae can support AcMNPV infections, there is an enormous variation among species with regard to mortality due to infection. Among species, the time between initial infection and virus induced death ranges from a few days to several weeks. In addition, results from laboratory studies have revealed that for susceptible hosts (e.g. *Trichoplusia ni, Heliothis virescens,* and *Spodoptera exidua*) a dozen or fewer polyhedra per insect may be sufficient to kill 50% or more of the larval population. In contrast, to achieve comparable mortality levels within populations of resistant hosts (e.g., *Helicoverpa zea*) each insect must ingest literally millions of polyhedra [Vail, P. V. and S. S. Collier. 1982. Comparative replication, mortality, and inclusion body production of the *Autographa californica* Nuclear Polyhedrosis Virus in *Heliothis* sp. *Ann. Entomol. Soc. Am.* 75:376–382; Vail, P. V. and Vail, S. V. 1987. Comparative replication of *Autographa californica* nuclear polyhedrosis virus in tissues of *Heliothis* spp. (Lepidoptera: Noctuidae). *Ann. Entomol. Soc. Amer.* 80:734–738].

Recent research efforts aimed at improving AcMNPV as a commercial microbial pesticide have focused primarily on reducing the time to death of infected hosts. The principal strategy employed for these efforts has been to genetically engineer AcMNPV recombinants that incorporate genes coding for invertebrate toxins and compounds that interfere with larval hormone function [Bonning, B. C. and Hammock, B. D. 1992. Development and potential of genetically engineered viral insecticides. *Biotechnology and Genetic Engineering Reviews* 10:455–489; Maeda, S. 1994. Expression of foreign genes in insect cells using baculovirus vectors. pp 1–31. In (K. Maramorosch and A. H. McIntosh, eds.), *Insect Cell Biotechnology,* CRC Press, Boca Raton, Fla.]. Recombinants expressing these substances have been shown to reduce larval feeding damage, and the first field trials of such recombinants recently have been approved by EPA. By comparison, little progress has been made toward the goal of expanding the host range of AcMNPV, in part because little is known about the mechanisms of resistance. Indeed, there is apparently no published description or explanation of the physiological basis for variation in susceptibility to fatal AcMNPV infections.

Thus, there remains a need for compositions and methods which enable effective control (e.g., reduction or eradication) of a wider variety of insect populations.

It is an object of the present invention to provide compositions and methods which do not suffer from the drawbacks of the heretofore-known compositions.

SUMMARY OF THE INVENTION

In accordance with the present invention, there are provided compositions and methods for use in controlling insect populations, wherein a first agent which suppresses insect immune function (as hereinafter defined) of a target insect is employed in conjunction with a second agent which is selected from the group consisting of insect pathogens (as hereinafter defined) for the target insect. In one preferred class of embodiments of the invention, the first agent is a polypeptide having immunosuppressive activity in the target insect or a polynucleotide sequence encoding the polypeptide; in the latter case, the polynucleotide may be conveniently administered to the target insect in a vector comprising the second agent (e.g., AcMNPV or similar insect pathogen).

BRIEF DESCRIPTION OF THE DRAWINGS

The invention may be better understood with reference to the accompanying drawings, in which.

DETAILED DESCRIPTION OF THE INVENTION

Figure 1:
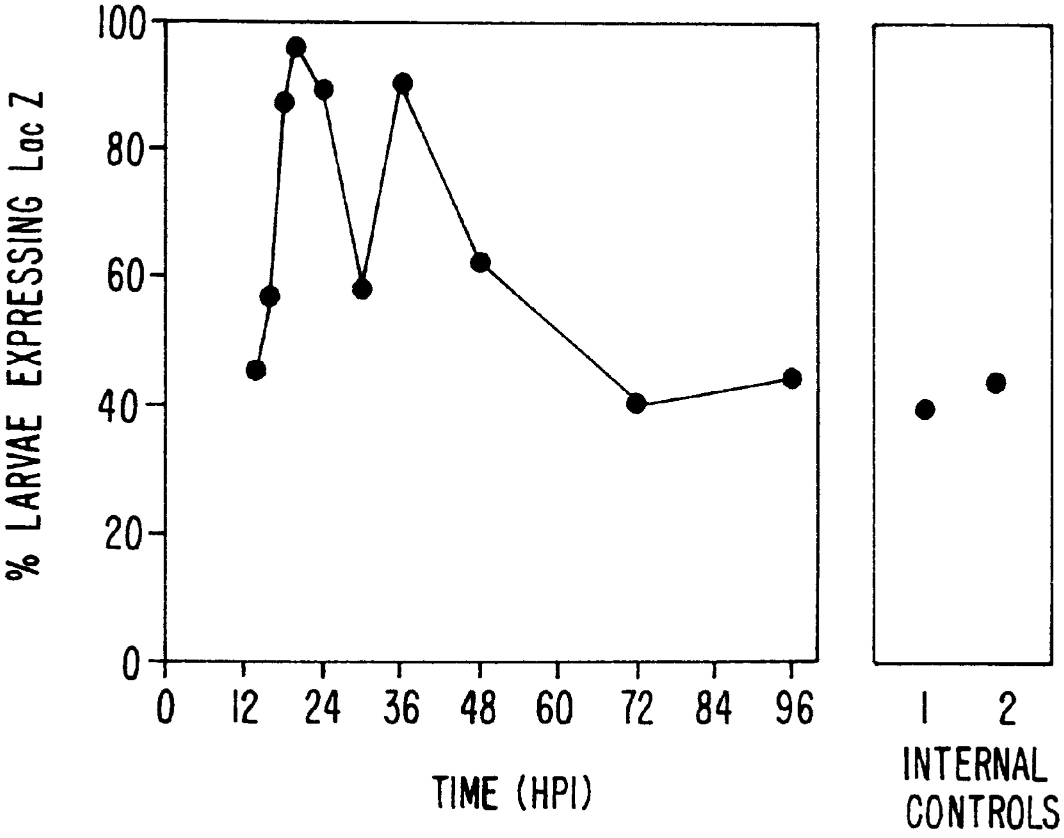
FIG. 1 illustrates the proportions of *H. zea* larvae expressing lacZ at various hpi (hours post inoculation) with 1100 polyhedra of AcMNPV-hsp70/lacZ.
Figure 2A:
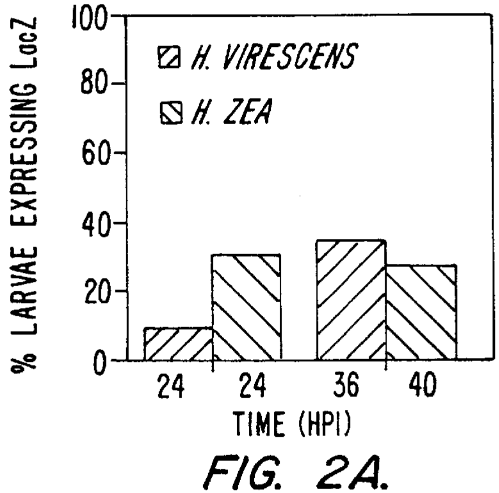
FIG. 2 illustrates comparisons of the proportions of lacZ expressing *H. virescens* and *H. zea* larvae and number of viral foci/infected insect sampled 24 to 40 hpi with 22 polyhedra of AcMNPV-hsp70/lacZ.
Figure 2B:
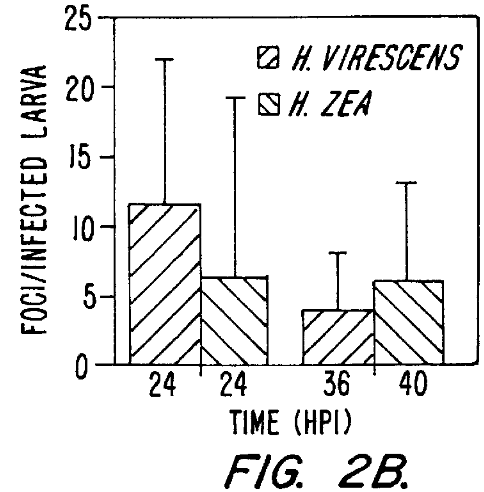
Figure 2C:
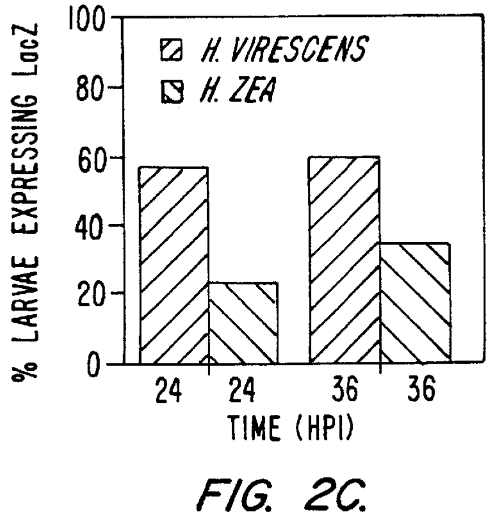
Figure 2D:
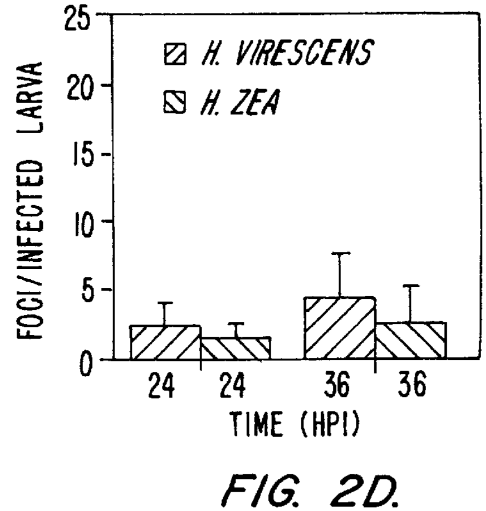

Pursuant to the present invention, compositions and methods are provided for use in controlling insect populations. The compositions of the present invention comprise in combination a first agent which suppresses insect immune function in an amount effective to suppress the immune function of a target insect and a second agent selected from the group consisting of insect pathogens in an amount effective to control or eliminate a population of the target insect. The methods of the present invention comprise administering to a target insect population the first agent before, after or simultaneously with the second agent.

The first agent suppresses insect immune function of a target insect. For purposes of the present invention, an agent which suppresses insect immune function may be defined as a composition which interferes with and prevents the completion of the encapsulation/melanization response which characterizes the known cellular immune response of insects to invading organisms or objects. Such composition disables the cellular immune response and prevents the host insect from successfully eliminating a foreign body (e.g., an insect pathogen).

Organic or inorganic chemical immunosuppressants, such as DDCA (diethyldithiocarbamic acid), PTU (phenylthiourea), benzamidine and other compounds [Saul, S. J. and Sugumaran, M. 1988. Prophenol oxidase activation in the hemolymph of *Sarcophaga bullata* larvae. *Arch. Insect Biochem. and Physiol.* 7:91–104] which interfere with components of the phenyloxidase system which is essential for successful activation and completion of the encapsulation response [Vinson, S. B. 1990. How parasitoids deal with the immune system of their host: an overview. *Arch. Insect Biochem. and Physiol.* 13:3–27 1990], may suitably be employed as first agents in accordance with the present invention. Use of DDCA in conjunction with an insect pathogen is illustrated in the examples herein.

Alternatively, the first agent is a polypeptide having immunosuppressive activity in the target insect. Examples of such peptides include VH1.1 and related gene products in the cysteine-rich gene family [Dib-Hajj, S. D., Webb, B. A., and Summers, M. D. 1993. Structure and evolutionary implications of a "cysteine-rich" *Campoletis sonorensis* polydnavirus gene family. *Proc. Natl. Acad. Sci.* USA 90:3765–3769] of the *Camplotetis sonorensis* polydnavirus. Complete nucleotide sequences for the genes encoding VH1.1 and related proteins in the family have been reported [Blissard, G. W., Theilmann, D. A. and Summers, M. D. 1980. Segment W of *Campoletis sonorensis* virus: expression, gene products, and organization. *Virology* 89:78–89; Theilmann, D. A. and Summers, M. D. 1988. Identification and comparison of *Campoletis sonorensis* virus transcripts expressed from four genomic segments in the insect hosts *Campoletis sonorensis* and *Heliothis virescens. Virology* 167:329–341].

The insect immunosuppressive agent is employed in conjunction with a second agent which is selected from the group consisting of insect pathogens for the target insect. For purposes of the present invention, an insect pathogen may be defined as an agent (such as a virus, bacterium, protozoan or fungus) which infects and causes disease symptoms in insects. Exemplary of an insect pathogen known to infect about 30 species of *lepidopterans* is AcMNPV. AcMNPV is the best studied of the baculoviruses, and its complete DNA sequence has been reported [Ayres, M. D., Howard, S. C., Kuzio, J., Lopez-Ferber, M. and Possee, R. D. 1994. The complete DNA sequence of *Autographia californica* nuclear polyhedrosis virus. *Virology* 202:586–605]. Other baculoviruses would also be suitable for use in accordance with the present invention, as would other insect pathogens effective (in conjunction with a first agent in accordance with the present invention) in killing or causing disease symptoms in a given target insect. The present invention has particular utility in those cases where a given insect pathogen for a given target insect in and of itself would not be completely effective in controlling the target insect population; the combination of first and second agents in such cases enables population control simply not practicable with agent alone.

In one preferred class of embodiments of the invention, the first agent is a polypeptide having immunosuppressive activity in the target insect and is provided in the form of a polynucleotide sequence encoding the polypeptide. The polynucleotide first agent is advantageously administered in accordance with this class of embodiments to the target insect in a vector comprising the second agent (e.g., AcMNPV or similar insect pathogen).

In a particularly preferred class of embodiments, a set of genetically engineered recombinants of AcMNPV is provided that expands the range of hosts that succumb to fatal viral infections. These recombinants comprise at least one polynucleotide sequence encoding a polypeptide insect immunosuppressant.

For any given combination of first and second agents, optimum amounts of a composition in accordance with the present invention for use in controlling a population of a given target insect may readily be determined empirically by quantifying dosage-mortality relationships within target insect populations. In general, the compositions of the present invention are administered to the target insect population in a manner known per se for administration of heretofore-known chemical and biological pesticides, for example by oral microinjection of inoculum in the laboratory or by spraying infested crop plants in the field. In addition to the first and second agents, the compositions of the present invention generally comprise a suitable carrier or excipient appropriate to the method of administration thereof, as would be readily appreciated by those working in the field.

Using the highly resistant and economically important host, *Helicoverpa zea,* as a model resistant species, a contributing factor to the physiological basis of viral resistance has been discovered and a means for circumventing it developed. Using a reporter gene construct of AcMNPV, the pathogenesis of viral infections in *H. zea,* an important agricultural pest reported to be highly resistant to infection by this baculovirus, has been examined. Specifically, it has been determined that *H. zea* larvae are actually very susceptible to initial infection by AcMNPV, but that the cellular immune response of *H. zea* is involved in stopping the spread and eliminating systemic AcMNPV infections. Further, it has been shown that down regulating the cellular immune response of *H. zea* results in the expansion of AcMNPV infections within host tissues. Because *H. zea* larvae are readily infected by AcMNPV, recombinant viruses are able to express these genes and thereby disable the immune response allowing infections to expand throughout the host tissues and ultimately to kill the insect. The early events during viral infection are very similar to those observed in a closely related but highly susceptible host, *H. virescens.*

The mechanism for resistance does not involve initial infection of the midgut epithelium following ingestion of virus; rather, an important mechanism contributing to viral resistance operates shortly after AcMNPV moves from the midgut epithelium to secondary target cells (i.e., tracheal epidermal cells of tracheae associated with the midgut). Microscopic analyses of viral plaques within the tracheal epidermis show that shortly after systemic AcMNPV infections are established, the cellular immune system of *H. zea* larvae is activated, and hemocytes begin aggregating at these sites of infections. Subsequently, melanization and encapsulation of the viral plaques and a cessation of viral spread through the tracheal system and into the other host tissues were observed. Characteristics to encapsulated viral foci are identical to those previously described for the cellular insect defense response to other pathogens and parasites.

These characteristics of AcMNPV infections have not heretofore been reported in any larval lepidopterans. In particular, the elimination of systemic AcMNPV infections, the decline in the proportion of infected insects following inoculation and the melanization/encapsulation immune response to baculovirus infection have not heretofore been described.

Using DDCA, it has been demonstrated in accordance with the present invention that in immunosuppressed larvae, both the proportion of infected insects and the size of individual viral foci it 48 hpi are greater in insects treated with the immunosuppressive agent compared to controls. Thus, the cellular immune response of *H. zea* and other lepidopteran species reported to be resistant to AcMNPV infection is a significant physiological mechanism contributing to resistance to baculovirus infection.

In accordance with one class of particularly preferred embodiments of the present invention, constructs of AcMNPV which contain polydnavirus genes which suppress the insect immune system are provided. Polydnaviruses, like AcMNPV, are double-stranded DNA viruses. Polydnaviruses are obligate symbionts associated with the calyx cells of the reproductive tracts of parasitic wasps such as *Camploetis sonorensis* (Ichneumonidae). They have a unique relationship both with the parasitic hymenoptera in which they are found and with the hosts that these wasps parasitize [Vinson, 1990, supra; Li, X. and Webb, B. A. 1994. Apparent functional role for a cysteine-rich polydnavirus protein in suppression of the insect cellular immune response. *J. Virology* 68:7482–7489]. Specifically, in order to complete their life cycle, these parasitoid wasps must incapacitate the immune system of their hosts (in this case larval lepidopterans) so that the immature stages of the wasp can complete development without being encapsulated by its host.

Since encapsulation is apparently the major host defense against parasitic egg invasion, host immunosuppression is usually attributed to the wasp's ability to avoid or suppress encapsulation. This immunosuppressive activity has been attributed to a family of virally encoded proteins that contain specific amino acid residues [Dibb-Hajj et al., 1993, supra; Li and Webb, 1994, supra].

Recently, one of these genes (VH1.1) originating from *Camplotetis sonorensis* polydnavirus was engineered into AcMNPV; the baculovirus was then used as a delivery system to test the hypothesis that the VH1.1 interferes with the encapsulation response of *H. virescens.* Experimental evidence demonstrated that encapsulation was significantly reduced relative to control insects [Li and Webb, 1994, supra]. Results from this study are significant, both in demonstrating an immunosuppressant function for the VH1.1 gene product, and in showing that a recombinant of AcMNPV containing VH1.1 expresses the gene product in amounts sufficient to suppress the cellular immune response of *H. virescens.* It was also found that immunosuppression by this construct was not effective in some larvae, suggesting that other genes may be necessary for complete elimination of the encapsulation response.

There are literally thousands of species of hymenoptera parasitoids that rely on larval lepidopteran hosts for their own development. Thus, there is a wealth of naturally-occurring polydnavirus genes coding for products with immunosuppressant function. Moreover, it is readily apparent that identification of useful modifications of such genes (e.g., mutations, deletions, genes encoding fusion proteins, etc.), as well as active fragments of such genes, would be well within the skill of those working in the field.

AcMNPV is widely used as an expression vector in cell culture, and is employed herein in the examples. Nonetheless, it would be readily apparent to those working in the field that the general principles described herein would be applicable to other insect pathogens which may serve as vector for one or more immunosuppressive genes. Examples of other insect pathogens which might serve as vectors for use in accordance with the present invention include, but are not limited to, other baculoviruses and other microorganisms pathogenic to a target insect population.

The invention may be better understood with reference to the accompanying examples, which are intended for purposes of illustration only and should not be construed as in any sense limiting the scope of the invention as defined in the claims appended hereto.

EXAMPLES

A single viral construct, AcMNPV-hsp70/lacZ, was employed in all of the examples. This recombinant contains all the genes found in wild type virus plus the *E. coli* b-galactosidase gene driven by the Drosophila heat shock promoter (hsp70). This reporter gene is expressed early in virus-infected cells [Engelhard, E. K., Kam-Morgan, L. N. W., Washburn, J. O., and Volkman, L. E. 1994. The insect tracheal system: a conduit for the systemic spread of *Autographa californica* M nuclear polyhedrosis virus. *Proc. Natl. Acad. Sci.* USA 91:3224–3227; Flipsen, J. T. M., Martens, J. W. M., van Oers, M. M., Vlak, J. M., and J. W. M. van Lent. 1994. Is replication of *Autographa californica* Nuclear Polyhedrosis Virus in the midgut epithelium of *Spodoptera exigua* larvae essential for systemic infection? 13th Annual ASV Meeting (abstract), p. 165]. Details on the construction and characterization of this recombinant have been reported [Engelhard et al., 1994, supra]. This reporter gene construct allowed tracking of the temporal spread of AcMNPV infections from infection of the first primary target cell in the midgut epithelium through to complete infection of the entire host larva.

Polyhedra of AcMNPV-hsp70/lacZ were used to infect test larvae in all experiments described here. Polyhedra were first isolated from liquefied cadavers of *T. ni* and partially purified by sucrose gradient centrifugation [Summers, M. D. and Smith, G. E. (1987). *A manual of methods for baculovirus vectors and insect cell culture procedures,* Texas Agricultural Experiment Station Bulletin No. 1555 (Tex. Agric. Exp. Stn., College Station, Tex.]. Pelleted polyhedra were suspended in a neutrally buoyant solution of glycerol and water (3:2 v/v). Viral inocula were quantified using a hemocytometer and held at 4° C. until use.

*Helicoverpa zea* and *Heliothis virescens* larvae were provided by American Cyanamid Corporation, Princeton, N.J. Prior to experimental procedures, all larvae were reared in cohorts on a synthetic diet [Tanada, Y. and G. Y. Chang. 1968. Resistance of the alfalfa caterpillar, *Colias eurytheme,* at high temperatures to a cytoplasmic-polyhedrosis virus and thermal inactivation point of the virus. J. Invertebr. Pathol. 10:79–83; Keddie, B. A. and L. E. Volkman. 1985. Infectivity difference between the two phenotypes of *Autographa californica* Nuclear Polyhedrosis Virus: importance of the 64K envelope glycoprotein. J. General Virol. 66:1195–2000] and maintained at 26±3° C. under constant light. In some cases prior to inoculation, larvae were refrigerated for 4 to 10 hours in order to regulate developmental rates; no effects of this procedure were detected in either viral susceptibility or pathogenesis. For all experiments, only third and fourth instars that were matched developmentally in their molt cycle were used. Quiescent, late second and third instar larvae that were preparing to molt were observed carefully in order to determine precisely when each individual shed its cuticle, the event used to define newly-molted third (3°) and fourth (4°) instar larvae.

All larvae were inoculated orally using a microapplicator (ISCO) fitted with a plastic tuberculin syringe (1 cc) with a 32 gauge needle. During inoculations, a blunt-tip needle was inserted through the mouth and into the anterior region of the larval midgut where polyhedra were delivered. Within experiments, both the volume and dosage were held constant, but among experiments, the inoculum volume was varied from 0.5 to 2.0 ml and the dosage from 17 to 1100 polyhedra per insect. Following injection, all test insects were maintained in individual containers at 28±1° C.

Larvae were sacrificed at various time intervals after inoculation, the specimens processed for lacZ expression and the distribution of the blue viral signal among host tissues determined as previously described [Engelhard et al., 1994, supra]. All whole mount and midgut preparations were examined for lacZ expression by stereo dissection (10–50×) and/or compound microscopy (100–480×). Discrimination of the viral signal between midgut epithelia and associated tracheal elements was facilitated by visual inspection of the intact tissue from various angles and by examination from the lumen side of the epithelium. For some *H. zea* whole mount specimens, pure midgut tissue free of basal lamina and tracheal elements was also isolated by infusing and incubating with dispase (Grade II, Boehringer Mannheim Biochemicals) for 20 to 30 min following the reported method [Engelhard, E. K., Keddie, B. A., and Volkman, L. E. 1991. Isolation of third, fourth and fifth instar larval midgut epithelia of the moth, *Trichoplusia ni. Tissue and Cell* 23, 917–928]; this procedure allowed differentiation of viral infection of the midgut epithelium from the associated tracheal epidermis. Endogenous b-galactosidase activity in the midgut epithelia of uninfected larvae of both species was detected within a ring of cells at the extreme anterior of the midgut at the junction with the foregut and in a ring of cells at the very posterior of the midgut at the junction with the hindgut.

Example 1

4° *H. zea* (N=92) were inoculated with 2200 polyhedra and sacrificed 14 to 168 hours post inoculation (hpi), processed for lacZ expression and the infection of specific larval tissues was determined. A control group of larvae also was injected with virus and allowed to continue development until either pupation or death.

No larvae exhibited lacZ expression at 14 hpi, but by 24 hpi small viral foci consisting of 1 to 3 cells were detested in the midgut epithelium and overlaying tracheal epidermis of test larva challenged with AcMNPV. At 48 hours post inoculation (hpi), 18 of 21 *H. zea* larvae (86%) expressed lacZ within the tracheal epidermis indicating the establishment of system viral infections, while only 23% of the internal control larvae died from infection. Fourteen of the lacZ-expressing larvae (67%) sacrificed at 48 hpi also showed varying levels of melanization along tracheae, and in some larvae, melanization was observed overlaying infected tracheal epidermis. Patches of melanization associated with tracheal vessels also were detected in 2 of the 3 larvae in which lacZ expression was not observed. In the 5 larvae (24%) with the most extensive infections (i.e., greatest lacZ expression), large viral plaques extended along tracheal branches encompassing most of the midgut, and there was little or no evidence of melanization. At 72 and 120 hpi, 18 and 20% of the sacrificed larvae (N=11 and 10 larvae, respectively) showed evidence of widespread systemic infections, and many exhibited melanized tracheae. In addition, clumps of hemocytes specifically associated with viral plaques were observed beginning as early as 24 hpi.

Results from this experiment suggested that AcMNPV infections in larvae of *H. zea* trigger the cellular immune response as indicated by melanization and encapsulation of viral infected cells; along tracheae. The cellular immune response of insects is well documented and if successful results in the encapsulation, melanization and elimination of eukaryotic and prokaryotic pathogens and parasites [Chapman, R. F. 1982. The insects: structure and function, 3rd ed. Harvard Univ. Press, Cambridge, Mass.; Vinson, 1990, supra]. There are apparently no published reports of this immune reaction in response to a baculovirus infection. It is also important to note that there had not heretofore been observed a melanization and encapsulation response within tissues of thousands of larvae of two susceptible hosts, *T. ni* and *H. virescens,* that were dissected and examined following inoculation with the same viral construct used in this experiment. These results provided the first empirical evidence that *H. zea* might be resistant to AcMNPV injection because of a specific cellular immune response which effectively eliminates systemic viral infections.

Example 2

3° *H. zea* (N=320) were inoculated with 1100 polyhedra and sacrificed 14 to 96 hpi, processed for lacZ expression and the infection of specific larval tissues was determined. Two control groups of larvae were also injected with virus and allowed to continue development until either pupation or death.

The second time course experiment was conducted in order to more carefully observe the interaction of AcMNPV with *H. zea*. In this experiment, cohorts of 20 or more larvae were sacrificed beginning 14 to 96 hpi. It was found that the proportion of infected insects rose rapidly between 14 and 24 hpi and ultimately reached 93%, a level significantly higher than the proportions of insects that ultimately died from virus in the internal control groups (circa 40%) (FIG. 1). In FIG. 1, each point represents a sample of 20 to 25 larvae. Internal control values represent the percent larvae dying with virus in two bioassays each containing 25 larvae. One internal control bioassay was established on each of the two days required to inoculate all test larvae (N=320).

As previously reported for *T. ni* and *H. virescens* [Engelhard et al., 1994, supra] and observed in Example 1, it was found in *H. zea* larvae that AcMNPV infections also progress directly from the midgut to the tracheal epidermis. At 30 hpi, the proportion of lacZ positive *H. zea* declined abruptly; this decrease in signaling insects does not represent an actual decline in the proportion of insects that are infected by AcMNPV but rather reflects the effects of the larval developmental state on expression of the reporter gene and the half life of its product. As a lepidopteran larva approaches the molt, it becomes quiescent, voids the contents of its alimentary canal and begins to form the new tissues of the next instar. During this transition period, the reporter gene signal is lost. In this study, the decline in lacZ positive *H. zea* coincided with the quiescent period prior to the molt to the fourth instar. At 36 hpi, the proportion of *H. zea* larvae with lacZ signals returned to a level (90%) comparable to that of insects sampled prior to the quiescent period. Between 36 and 72 hpi, however, the proportion of signaling insects declined rapidly to approximately 40% which was predictive of the final mortality.

These results on the temporal pattern of lacZ expression in *H. zea* larvae are highly significant for several reasons. First, during the first 24 hpi, the proportions of signaling *H. zea* (reported to be a highly "resistant" species) and the tissue-specific distribution of AcMNPV were very similar to those documented in the highly susceptible and closely-related host species, *H. virescens.* Second, the proportion of *H. zea* larvae with AcMNPV infections in their tracheal system immediately prior to and after the molt, was not predictive of the mortality in the internal control groups. Thus, it appears that some *H. zea* larvae "cured" their infections. This phenomenon has not been observed in *T. ni* and *H. virescens* infected with AcMNPV; in these hosts the proportion of larvae expressing lacZ within the tracheal system prior to the molt accurately predicts the final mortality from virus.

In addition to the temporal differences in the proportions of infected *H. zea* described above, profound differences were found in the appearance and growth of viral plaques in this host compared to *H. Virescens* and *T. ni*. As early as 30 hpi, evidence of melanization specifically associated with viral signals within the tracheal epidermis was found. When larval tissues from larvae sacrificed at 20 hpi were excised and examined under compound microscopy (100–400×), hemocytes were found adhering to viral plaques in the tracheal epidermis. In addition, small areas of melanization were observed within foci with very dark lacZ signals suggesting that proportions of larvae with melanization may have been more common than determined from whole mounts observed at 10–50×. For some encapsulated foci, lacZ signals were also evident within aggregated hemocytes suggesting that either the hemocytes were infected by virus or the hemocytes were phagocytosing infected cells or viral products from infected cells. Importantly, between 30 and 96 hpi, there was little expansion in the average size of viral plaques within the tracheal epidermis; this is in striking contrast to the rapid and continual expansion of viral plaques within the same tissues of *H. virescens* and *T. ni* [Engelhard et al., 1994, supra]. Results on the pathogenesis of AcMNPV infections in *H. zea* larvae in Example 2 were consistent with those from Example 1 and support the hypothesis that the cellular immune response of larvae blocks the spread of virus through host tissues.

Example 3

Experiments were conducted comparing early infection of 4° *H. virescens* (N=94 and 125) and *H. zea* (N=108 and 137). In this experiment, it was sought to compare the early pathogenesis of AcMNPV infections between *H. virescens* and *H. zea,* species reported to be highly susceptible and highly resistant, respectively. The objective was to determine if there were differences in the pattern of midgut infections, the primary target tissue of ingested virus, that might contribute to the published reports of significant differences in dose-mortality relationships between species. Pathogenesis was assessed by challenging 4° *H. zea* and *H. virescens* with the same inoculum of AcMNPV and subsequently comparing the proportions of infected insects and the number of viral foci per infected insect. Larvae were sacrificed at 24 and 36–40 hpi in order to assess AcMNPV distribution early in the systemic infection of hosts.

In both experiments, almost no differences were found between the two species in the proportion of infected insects (FIG. 2), and there were no significant differences between the mean number of foci per infected insect at either time point in either experiment (ANOVA, $p > 0.05$). 4° larvae of both species were inoculated, and results from two independent experiments (above and below) are shown. Each histogram represents the mean value determined from a cohort of 24 to 32 inoculated larvae; lines above bars on the right represent one standard deviation of the mean.

Results from this experiment clearly demonstrate that *H. zea* is actually very similar to *H. virescens* with regard to susceptibility to AcMNPV infection. Moreover, the results show that resistance to viral-induced mortality in *H. zea* does not involve the infection of the midgut epithelium; rather the mechanism of resistance operates after infections have entered the tracheal system of the host.

Example 4

An experiment was conducted using a compound, diethyldithio-carbamic acid (DDCA), known to inactivate the cellular immune response of insects. 3° (N=29) and 4° (N=29) *H. zea* were inoculated with virus, injected intrahemocoelically with DDCA at 15 to 24 hpi and subsequently processed for viral signal at 48 hpi. A group of insects of each developmental stage, inoculated with virus but not DDCA, served as controls.

By using DDCA to immunosuppress *H. zea*, the hypothesis that the larval immune system is responsible for halting the spread of AcMNPV infections was tested. 3° and 4° *H. zea* were inoculated with AcMNPV and between 15 and 24 hpi, injected either 0.01 or 0.001 mg of DDCA into the hemocoels of test larvae. These larvae were sacrificed at 48 hpi, and the proportions of infected insects and the size of viral foci were compared with control larvae inoculated with the same amount of virus but not injected with DDCA. A time point of 48 hpi was chosen because results from Examples 1 and 2 (see FIG. 1) showed that within cohorts sampled at this time, the proportion of AcMNPV infected larvae had declined relative to previous levels (e.g. at 24 hpi), and in many larvae there was evidence of melanization and a cessation of viral spread.

Figure 3:
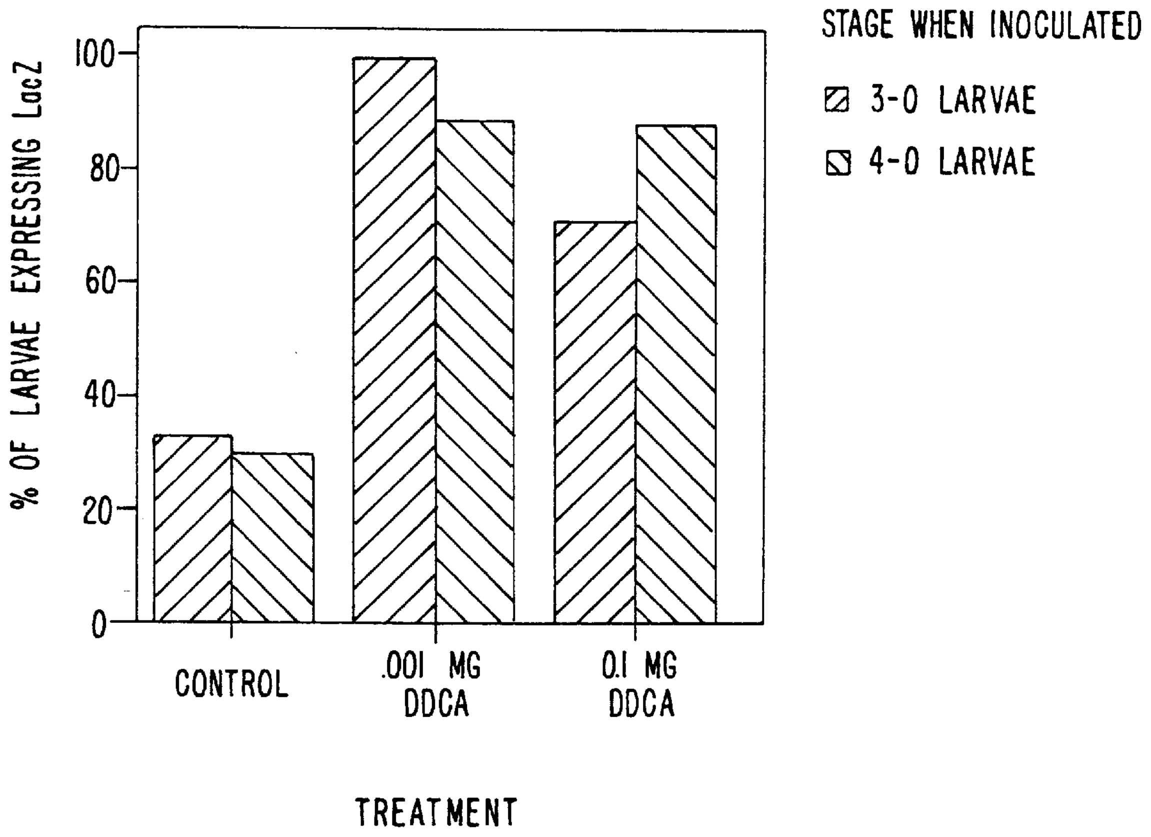
FIG. 3 illustrates the proportion of *H. zea* larvae expressing lacZ 48 hpi with 110 polyhedra of AcMNPV-hsp70/lacZ.

Results comparing the proportions of insects signaling lacZ at 48 hpi are shown in FIG. 3. Each bar represents the proportion of signaling insects from a population of 7 to 12 insects. For both third and fourth instar larvae inoculated with virus and DDCA, greater proportions of larvae expressing lacZ were found compared to control insects. In addition, there were striking differences in the distribution and size of viral plaques in DDCA treated insects compared to controls. Among controls, individual viral foci were very small, each typically consisting of less than 10 infected tracheal epidermal cells; the largest plaques covered less than 5% of the tracheal vessels associated with the midgut and many larvae exhibited patches of melanization along infected tracheae. In contrast, among DDCA treated larvae, significantly larger viral plaques were found compared to developmentally-matched controls. In some DDCA treated larvae, the entire tracheal systems associated with the midgut were infected with virus. Large viral plaques covering 10 to 40% of the midgut tracheae also were observed in other specimens, and there were fewer insects showing evidence of melanization compared to controls. These results are highly significant because they indicate that when the immune system of *H. zea* is chemically suppressed, both the proportion of infected insects and the extent of viral infections are greater compared to controls. The most reasonable explanation for these findings is that the immune system is responsible for at least part of the resistance in *H. zea* to AcMNPV infections.

Example 5

In this experiment, quiescent second (N=60) and third instar (N=58) *H. zea* larvae that were preparing to molt were exposed to female *Campoletis sonorensis* wasps which were observed to oviposit into the larvae. Immediately upon molting to the third or fourth instar, each *H. zea* caterpillar was inoculated with approximately 20 polyhedra of AcMNPV-hsp70/lacZ. An additional 10 4° larvae were parasitized by *C. sonorensis* but not inoculated with virus, and 25 4° larvae were inoculated with virus but not exposed to ovipositing wasps; these insects serve as controls for comparing the tissue specific expression of lacZ with larvae parasitized by *C. sonorensis* and infected with AcMNPV. *H. zea* are sacrificed at time points beginning 96 hpi and processed for elucidation of the lacZ reporter signal.

At 48 hours after oviposition parasitized *H. zea* were dissected and the condition of parasitoid eggs within the host hemolymph determined. None of the eggs showed evidence of colocalized melanization, and the embryonic wasps appeared to be developing normally. Thus, it appears that *H. zea* is a suitable host for *C. sonorensis,* and *C. sonorensis* does in fact immunosuppress *H. zea.*

Comparison of lacZ signal patterns in parasitized and unparasitized larvae confirms the role of the cellular immune system in stopping the spread and eliminating AcMNPV infections in this host. Specifically, a greater proportion of parasitized larvae expressing lacZ compared to unparasitized larvae is observed. In addition, the lacZ signal is more widely distributed in parasitized, virus-infected larvae compared to unparasitized, virus-infected larvae.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. An isolated baculovirus comprising a heterologous polynucleotide construct encoding a polypeptide which suppresses target lepidopteran insect cellular immune response, where the heterologous polynucleotide construct is linked for expression to a promoter operative early in the baculoviral replication cycle in baculovirus-infected cells; wherein the polypeptide in the target lepidopteran insect suppresses melanization and encapsulation functions in the target lepidopteran insect with a result identical to suppression effected by a VH1.1 polypeptide in *Helicoverpa zea;* whereby the cellular immune response of suppression of melanization and encapsulation function(s) enhances baculoviral infection of target lepidopteran insects resistant to infection by baculovirus.

2. The baculovirus of claim 1, wherein the baculovirus encodes an *Autographa californica* M Nucleopolyhedrosis Virus (AcMNPV).

3. The baculovirus of claim 1, wherein the heterologous polynucleotide sequence encodes an immunosuppressive polypeptide from a polydnavirus.

4. The baculovirus of claim 3, wherein the polydnavirus is a *Campoletis sonorensis* polydnavirus.

5. The baculovirus of claim 1, wherein the heterologous polynucleotide sequence is a VH1.1 gene.

6. An isolated baculovirus genome comprising a heterologous polynucleotide construct encoding a polypeptide which suppresses target lepidopteran insect cellular immune response where the heterologous polynucleotide is linked for expression to a promoter operative early in the baculoviral replication cyle in baculovirus-infected cells; wherein the polypeptide in the target lepidopteran insect suppresses melanization and encapsulation function(s) in the target lepidopteran insect with a result identical to suppression effected by the VH1.1 polypeptide in *Helicoverpa zea;* whereby the cellular immune response of suppression of melanization encapsulation function(s) enhances baculoviral infection of target lepidopteran insects resistant to infection by baculovirus.

7. The baculovirus genome of claim 6, which is a *Autographa californica* M Nucleopolyhedrosis Virus (AcMNPV) genome.

8. The baculovirus genome of claim 6, wherein the heterologous polynucleotide sequence encodes an immunosuppressive polypeptide from a polydnavirus.

9. The baculovirus genome of claim 8, wherein the polydnavirus is a *Campoletis sonorensis* polydnavirus.

10. The baculovirus genome of claim 6, wherein the heterologous polynucleotide sequence is a VH1.1 gene.

11. A method of enhancing infection of a target lepidopteran insect by a baculovirus, the method comprising the steps of:

(i) contacting the target lepidopteran insect with an isolated baculovirus comprising a heterologous polynucleotide construct encoding a polypeptide which suppresses target lepidopteran insect cellular immune response where the heterologous polynucleotide construct is linked for expression to a promoter operative in baculovirus infected cells; wherein the polypeptide in the target lepidopteran insect suppresses the melanization and encapsulation function(s) in the target lepidopteran insect with a result identical to the suppression effected by a VH1.1 polypeptide in *Helicoverpa zea;* whereby the cellular immune response of suppression of melanization and encapsulation function (s) enhance baculoviral infection of target lepidopteran insects resistant to infection by baculovirus, and (ii) effecting expression of the polypeptide which suppresses target lepidopteran insect cellular immune response in the target lepidopteran insect, suppressing the target lepidopteran insect cellular immune response and thereby enhancing baculoviral infection in a target resistant lepidopteran insect resistant to infection by baculovirus.

12. The method of claim 11, wherein the baculovirus is *Autographa californica* M Nucleopolyhedrosis Virus (AcMNPV).

13. The method of claim 11, wherein the heterologous polynucleotide sequence encodes an immunosuppressive polypeptide from a polydnavirus.

14. The method of claim 13, wherein the polydnavirus is a *Campoletis sonorensis* polydnavirus.

15. The method of claim 11 wherein the heterologous polynucleotide sequence is a VH1.1 gene.

16. The method of claim 11, wherein the target insect is *Helicoverpa zea.*

* * * * *